(12) United States Patent
Li et al.

(10) Patent No.: US 8,063,072 B2
(45) Date of Patent: Nov. 22, 2011

(54) HETEROCYCLIC ANTIVIRAL COMPOUNDS

(75) Inventors: Jim Li, San Francisco, CA (US); Javier de Vincente Fidalgo, Glen Ridge, NJ (US); Ryan Craig Schoenfeld, Basking Ridge, NJ (US); Francisco Xavier Talamas, Livingston, NJ (US)

(73) Assignee: Roche Palo Alto LLC, South San Francisco, CA (US)

( * ) Notice: Subject to any disclaimer, the term of this patent is extended or adjusted under 35 U.S.C. 154(b) by 0 days.

(21) Appl. No.: 12/887,450

(22) Filed: Sep. 21, 2010

(65) Prior Publication Data

US 2011/0070189 A1    Mar. 24, 2011

Related U.S. Application Data

(60) Provisional application No. 61/244,287, filed on Sep. 21, 2009.

(51) Int. Cl.
 *A01N 43/40* (2006.01)
 *A61K 31/44* (2006.01)
 *C07D 421/00* (2006.01)
(52) U.S. Cl. ...... 514/332; 514/277; 546/255; 546/268.1
(58) Field of Classification Search .............. 546/255, 546/268.1; 514/277, 332
See application file for complete search history.

(56) References Cited

U.S. PATENT DOCUMENTS

| 2010/0010017 A1 | 1/2010 | Liu et al. |
| 2010/0021423 A1 | 1/2010 | Brameld et al. |
| 2010/0081658 A1 | 4/2010 | Chin et al. |
| 2010/0111900 A1 | 5/2010 | Li et al. |
| 2010/0158860 A1 | 6/2010 | Steiner et al. |

FOREIGN PATENT DOCUMENTS

| WO | WO 01/85172 A1 | 11/2001 |
| WO | WO 01/85172 A2 | 11/2001 |
| WO | WO 2004/041818 A1 | 5/2004 |
| WO | WO 2009/032116 A1 | 3/2009 |
| WO | WO 2009/032123 A1 | 3/2009 |
| WO | WO 2009/032123 A2 | 3/2009 |
| WO | WO 2009/032123 A3 | 3/2009 |
| WO | WO 2009-032125 A1 | 3/2009 |
| WO | WO 2009/039127 A1 | 3/2009 |
| WO | WO 2009/039134 A1 | 3/2009 |
| WO | WO 2009/039135 A1 | 3/2009 |
| WO | WO 2009/064848 A1 | 5/2009 |
| WO | WO 2009/064852 A1 | 5/2009 |
| WO | WO 2010/111436 A2 | 9/2010 |
| WO | WO 2010/111437 A1 | 9/2010 |

*Primary Examiner* — Paul V. Ward

(74) *Attorney, Agent, or Firm* — Brian L. Buckwalter

(57) ABSTRACT

Compounds having the formula I wherein $R^1$, $R^2$, $R^3$, $R^4$, and $R^5$ are as defined herein are Hepatitis C virus NS5b polymerase inhibitors. Also disclosed are compositions and methods for treating an HCV infection and inhibiting HCV replication.

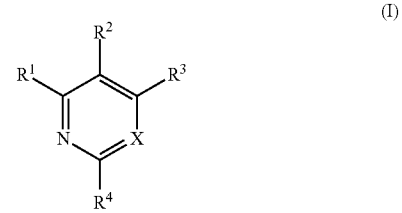

(I)

16 Claims, No Drawings ial RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

HETEROCYCLIC ANTIVIRAL COMPOUNDS

CROSS REFERENCE TO PRIOR APPLICATIONS

This application claims the benefit of priority to U.S. Ser. No. 61/244,287 filed Sep. 21, 2009 which is hereby incorporated by reference in their entirety.

FIELD OF THE INVENTION

The present invention provides non-nucleoside compounds of formula I, and certain derivatives thereof, which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.,* 1999 19:5; Di Besceglie, A. M. and Bacon, B. R., *Scientific American,* October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.-Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase.

The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH50304 (Broceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential.

The present invention provides a compound according to formula I, or a pharmaceutically acceptable salt thereof wherein R1, R2, R3, R4, R5 are as follows:

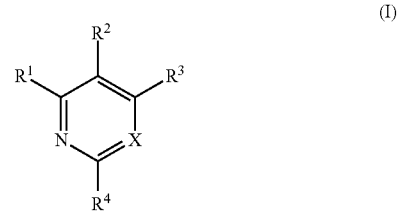

X is N or $CR^5$;
$R^1$ is a heteroaryl radical selected from the group consisting of A-1, A-2, A-3 and A-4 said heteroaryl being optionally substituted by halogen, $C_{1-6}$ alkyl, $C_{1-3}$ haloalkyl, $C_{1-6}$ alkoxy:

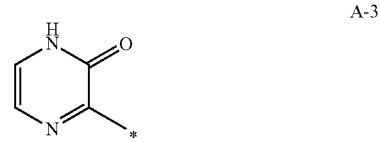

$R^2$ is hydrogen, cyano or hydroxyl;
$R^3$ is CH=CHAr, $[C(R^6)_2]_n$, naphthyl or $C(=O)X^2$ wherein Ar is phenyl and said phenyl or said naphthyl are optionally independently substituted with one to three substitutents selected from the group consisting of (a) hydroxy, (b) $C_{1-6}$ alkoxy, (c) $C_{1-6}$ alkyl, (d) $C_{1-10}$ hydroxyalkyl wherein one or two carbon atoms optionally can be replaced by oxygen provided that the replacement does not form a oxygen-oxygen bond, (e) $C_{1-3}$ alkoxy-$C_{1-6}$ alkyl, (f) halogen, (g) cyano, (h) $C_{1-6}$ alkoxycarbonyl, (i) $C_{1-6}$ alkylsulfonyl, (j) $X^1(CH_2)_{1-}$ wherein $X^1$ is O, $NR^6$ or a bond, (k) $C_{1-3}$ acylamino-$C_{1-6}$ alkyl, (l) $(CH_2)_nNR^aR^b$ wherein n is zero to two, and (m) carboxyl;
$R^a$ and $R^b$ are (i) independently in each occurrence (a) hydrogen, (b) $C_{1-6}$ alkyl, (c) $C_{1-6}$ alkylsulfonyl, (d) $C_{1-6}$ acyl, (e) $C_{1-6}$ haloalkylsulfonyl, (f) $C_{3-7}$ cycloalkylsulfonyl, (g) $C_{3-7}$ cycloalkyl-$C_{1-3}$ alkyl-sulfonyl, (h) $C_{1-6}$ alkoxy-$C_{1-6}$ alkylsulfonyl, (i) $SO_2NR_6$ or (k) $C_{1-6}$ haloalkyl;

$X^2$ is OH, $C_{1-6}$ alkoxy or $NR^cR^d$;

$R^c$ and $R^d$ are (i) independently in each occurrence hydrogen, $C_{1-6}$ alkyl or $C_{4-6}$ cycloalkyl or (ii) taken together with the nitrogen to which they are attached are a cyclic amine wherein the cycloalkyl or cyclic amine moiety is substituted by $(CH_2)NR^aR^b$ wherein n is zero to two;

$R^4$ is hydrogen, $C_{1-6}$ alkyl, $C_{1-6}$ haloalkyl, or $CR^{4a}R^{4b}R^{4c}$ wherein (i) $R^{4a}$, $R^{4b}$ and $R^{4c}$ are independently selected from $C_{1-3}$ alkyl, $C_{1-2}$ alkoxy, $C_{1-3}$ fluoroalkyl, $C_{1-3}$ hydroxyalkyl, cyano or hydroxy; or (ii) when taken together, $R^{4a}$ and $R^{4b}$ together are $C_{2-4}$ alkylene and $R^{4c}$ is hydrogen, $C_{1-3}$ alkyl, $C_{1-2}$ alkoxy, halogen, $C_{1-3}$ hydroxyalkyl, cyano or $C_{1-3}$ fluoroalkyl;

$R^5$ is hydrogen, $C_{1-6}$ alkoxy, halogen or $C_{1-6}$ alkyl;

$R^6$ is independently in each occurrence hydrogen or $C_{1-3}$ alkyl; or, a pharmaceutically acceptable salt thereof.

The present invention also provides a method for treating a disease a Hepatitis C Virus (HCV) virus infection by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ------ " drawn through a bond each refer to the point of attachment of a functional group or other chemical moiety to the rest of the molecule of which it is a part. Thus, for example:

$MeC(\!\!=\!\!O)OR^4$ wherein

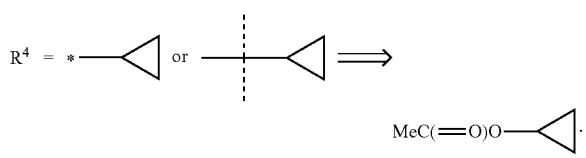

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—)

tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In one embodiment of the present invention there is provided a compound according to formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above. The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

In a second embodiment of the present invention there is provided a compound according to formula I wherein X is $CR^5$; $R^5$ is hydrogen; $R^3$ is CH=CHAr or $[C(R^6)_2]_n$ wherein n is two; Ar is optionally substituted p-phenylene-$(NR^aR^b)$; and, $R^4$ is hydrogen, $C_{1-6}$ alkyl, $C_{1-6}$ haloalkyl, or $CR^{4a}R^{4b}R^{4c}$ wherein: (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl; or a pharmaceutically acceptable salt thereof.

In a third embodiment of the present invention there is provided a compound according to formula I wherein X is $CR^5$; $R^5$ is hydrogen; $R^1$ is 2-oxo-1,2-dihydro-pyridin-3-yl optionally substituted by halogen, $C_{1-6}$ alkyl, $C_{1-3}$ haloalkyl, $C_{1-6}$ alkoxy, $X^1$—$(CH_2)_{1-6}CO_2H$ or $X^1$—$(CH_2)_{2-6}NR^eR^f$ wherein $X^1$ is O, $NR^6$ or a bond; $R^3$ is CH=CHAr or $[C(R^6)_2]_n$ wherein n is two; Ar is optionally substituted p-phenylene-$(NR^aR^b)$; and, $R^4$ is $CR^{4a}R^{4b}R^{4c}$ wherein $R^{4a}$, $R^{4b}$ and $R^{4c}$ are independently $C_{1-3}$ alkyl; or a pharmaceutically acceptable salt thereof.

In a another embodiment of the present invention there is provided a compound according to formula I wherein X is $CR^5$; $R^5$ is hydrogen; $R^1$ is 2-oxo-1,2-dihydro-pyridin-3-yl optionally substituted by halogen, $C_{1-6}$ alkyl, $C_{1-3}$ haloalkyl, $C_{1-6}$ alkoxy, $X^1$—$(CH_2)_{1-6}CO_2H$ or $X^1$—$(CH_2)_{2-6}NR^eR^f$ wherein $X^1$ is O, $NR^6$ or a bond; $R^3$ is CH=CHAr or $[C(R^6)_2]_n$ wherein n is two; Ar is optionally substituted p-phenylene-$(NR^aR^b)$; and, $R^4$ is $CR^{4a}R^{4b}R^{4c}$ wherein $R^{4a}$ and $R^{4b}$ together are $C_{2-4}$ alkylene and $R^{4c}$ is hydrogen, $C_{1-3}$ alkyl, $C_{1-2}$ alkoxy, halogen, $C_{1-3}$ hydroxyalkyl, cyano or $C_{1-2}$ fluoroalkyl; or a pharmaceutically acceptable salt thereof.

In yet another embodiment of the present invention there is provided a compound according to formula I wherein X is $CR^5$; $R^5$ is hydrogen; $R^1$ is 2-oxo-1,2-dihydro-pyridin-3-yl optionally substituted by halogen, $C_{1-6}$ alkyl, $C_{1-3}$ haloalkyl, $C_{1-6}$ alkoxy, $X^1$—$(CH_2)_{1-6}CO_2H$ or $X^1$—$(CH_2)_{2-6}NR^eR^f$ wherein $X^1$ is O, $NR^6$ or a bond; $R^3$ 2-naphthyl optionally substituted p-phenylene-$(NR^aR^b)$; and, $R^4$ is $CR^{4a}R^{4b}R^{4c}$ wherein $R^{4a}$, $R^{4b}$ and $R^{4c}$ are independently $C_{1-3}$ alkyl; or a pharmaceutically acceptable salt thereof.

In a fourth embodiment of the present invention there is provided a compound according to formula I wherein X is $CR^5$; $R^5$ is hydrogen; $R^1$ is 2-oxo-1,2-dihydro-pyridin-3-yl optionally substituted by halogen, $C_{1-6}$ alkyl, $C_{1-3}$ haloalkyl, $C_{1-6}$ alkoxy, $X^1$—$(CH_2)_{1-6}CO_2H$ or $X^1$—$(CH_2)_{2-6}NR^eR^f$ wherein $X^1$ is O, $NR^6$ or a bond; $R^3$ is CH=CHAr; Ar is optionally substituted p-phenylene-$(NR^aR^b)$; $R^a$ is hydrogen and $R^b$ is $C_{1-6}$ alkylsulfonyl; and, $R^4$ is $CR^{4a}R^{4b}R^{4c}$ wherein $R^{4a}$, $R^{4b}$ and $R^{4c}$ are independently $C_{1-3}$ alkyl; or a pharmaceutically acceptable salt thereof.

In a another embodiment of the present invention there is provided a compound according to formula I wherein X is $CR^5$; $R^5$ is hydrogen; $R^1$ is 2-oxo-1,2-dihydro-pyridin-3-yl optionally substituted by halogen, $C_{1-6}$ alkyl, $C_{1-3}$ haloalkyl, $C_{1-6}$ alkoxy, $X^1$—$(CH_2)_{1-6}CO_2H$ or $X^1$—$(CH_2)_{2-6}NR^eR^f$ wherein $X^1$ is O, $NR^6$ or a bond; $R^3$ is CH=CHAr; Ar is optionally substituted p-phenylene-$(NR^aR^b)$; $R^a$ is hydrogen and $R^b$ is $C_{1-6}$ haloalkyl, $C_{1-6}$ alkylsulfonyl, $C_{1-6}$ acyl, $C_{1-6}$ haloalkylsulfonyl or $C_{3-7}$ cycloalkylsulfonyl; and, $R^4$ is $CR^{4a}R^{4b}R^{4c}$ wherein $R^{4a}$, $R^{4b}$ and $R^{4c}$ are independently $C_{1-3}$ alkyl; or a pharmaceutically acceptable salt thereof.

In a fifth embodiment of the present invention there is provided a compound according to formula I wherein X is $CR^5$; $R^5$ is hydrogen; $R^3$ is $R^3$ is $C(=O)X^2$; $X^2$ is OH, $C_{1-6}$ alkoxy or $NR^cR^d$; and $R^4$ is hydrogen, $C_{1-6}$ alkyl, $C_{1-6}$ haloalkyl, or $CR^{4a}R^{4b}R^{4c}$ wherein: (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl; or a pharmaceutically acceptable salt thereof.

In a sixth embodiment of the present invention there is provided a compound according to formula I wherein X is $CR^5$; $R^5$ is hydrogen; $R^3$ is $R^3$ is $C(=O)X^2$; $X^2$ is $NR^cR^d$ and wherein $R^c$ is hydrogen and $R^d$ is a $C_{4-6}$ cycloalkyl substituted by $(CH_2)_nNR^aR^b$ wherein n is zero to two; and $R^4$ is hydrogen, $C_{1-6}$ alkyl, $C_{1-6}$ haloalkyl, or $CR^{4a}R^{4b}R^{4c}$ wherein: (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl; or a pharmaceutically acceptable salt thereof.

In a another embodiment of the present invention there is provided a compound according to formula I wherein X is $CR^5$; $R^5$ is hydrogen; $R^3$ is $R^3$ is $C(=O)X^2$; $X^2$ is $NR^cR^d$ wherein $R^c$ is hydrogen and $R^d$ is a $C_{4-6}$ cycloalkyl substituted by $(CH_2)_nNR^aR^b$ wherein n is zero to two; and $R^4$ is $CR^{4a}R^{4b}R^{4c}$ wherein $CR^{4a}R^{4b}$ and $R^{4c}$ are independently $C_{1-3}$ alkyl, or a pharmaceutically acceptable salt thereof.

In a seventh embodiment of the present invention there is provided a compound according to formula I wherein X is $CR^5$; $R^5$ is hydrogen; $R^3$ is optionally substituted naphthyl; and, $R^4$ is hydrogen, $C_{1-6}$ alkyl, $C_{1-6}$ haloalkyl, or $CR^{4a}R^{4b}R^{4c}$ wherein: (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl; or a pharmaceutically acceptable salt thereof.

In a eighth embodiment of the present invention there is provided a compound according to formula I wherein X is $CR^5$; $R^5$ is hydrogen; $R^3$ is 6-methanesulfonylamino-naphthalen-2-yl; and, $R^4$ is hydrogen, $C_{1-6}$ alkyl, $C_{1-6}$ haloalkyl, or $CR^{4a}R^{4b}R^{4c}$ wherein: (i) $CR^{4a}R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl; or a pharmaceutically acceptable salt thereof.

In a ninth embodiment of the present invention there is provided a compound according to formula I wherein X is N; $R^1$ is a heteroaryl radical selected from the group consisting of 2-oxo-1,2-dihydro-pyridin-3-yl, 3-oxo-3,4-dihydro-pyrazin-2-yl, 3-oxo-2,3-dihydro-pyridazin-4-yl, optionally substituted by halogen, $C_{1-6}$ alkyl, $C_{1-3}$ haloalkyl, $C_{1-6}$ alkoxy, $X^1$—$(CH_2)_{1-6}CO_2H$ or $X^1$—$(CH_2)_{2-6}NR^eR^f$ wherein $X^1$ is O, $NR^6$ or a bond; $R^3$ is CH=CHAr; Ar is optionally substituted p-phenylene-$(NR^aR^b)$; and, $R^4$ is hydrogen, $C_{1-6}$ alkyl, $C_{1-6}$ haloalkyl, or $CR^{4a}R^{4b}R^{4c}$ wherein: (i) $CR^{4a}R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl; or a pharmaceutically acceptable salt thereof.

In a tenth embodiment of the present invention there is provided a compound selected from I-1 to I-7 in TABLE I.

In a eleventh embodiment of the present invention there is provide a method of treating a HCV infection in a patient in need thereof comprising administering a therapeutically effective amount of a compound according to formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above.

In a twelfth embodiment of the present invention there is provide a method of treating a HCV infection in a patient in need thereof comprising co-administering a therapeutically effective amount of a compound according to formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above and at least one immune system modulator and/or at least one antiviral agent that inhibits replication of HCV.

In a thirteenth embodiment of the present invention there is provide a method of treating a disease caused by HCV in a patient in need thereof comprising co-administering a therapeutically effective amount of a compound according to formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above and at least one immune system modulator selected from interferon, interleukin, tumor necrosis factor or colony stimulating factor.

In a fourteenth embodiment of the present invention there is provide a method of treating a HCV infection in a patient in need thereof comprising co-administering a therapeutically effective amount of a compound according to formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above and an interferon or chemically derivatized interferon.

In a fifteenth embodiment of the present invention there is provide a method of treating a HCV infection in a patient in need thereof comprising co-administering a therapeutically effective amount of a compound according to formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In a sixteenth embodiment of the present invention there is provided a method for inhibiting viral replication in a cell by delivering a therapeutically effective amount of a compound of the formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above admixed with at least one pharmaceutically acceptable carrier, diluent or excipient.

In a seventeenth embodiment of the present invention there is provided a composition comprising a compound according to formula I wherein $R^1$, $R^2$, $R^3$, $R^4$, $R^{4a}$, $R^{4b}$, $R^{4c}$, $R^5$, $R^6$, $R^a$, $R^b$, $R^c$, $R^d$, $R^e$, $R^f$, Ar, X, $X^1$, $X^2$ and n are as defined herein above with at least one pharmaceutically acceptable carrier, diluent or excipient.

The term "alkyl" as used herein without further limitation alone or in combination with other groups, denotes an unbranched or branched chain, saturated, monovalent hydrocarbon residue containing 1 to 10 carbon atoms. "$C_{1-6}$ alkyl" as used herein refers to an alkyl composed of 1 to 6 carbons.

Examples of alkyl groups include, but are not limited to, lower alkyl groups include methyl, ethyl, propyl, iso-propyl, n-butyl, iert-butyl, tert-butyl, neopentyl, hexyl, and octyl. Any carbon hydrogen bond can be replaced by a carbon deuterium bond with departing from the scope of the invention.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term (ar)alkyl refers to either an unsubstituted alkyl or an aralkyl group. The term (hetero)aryl or (hetero)aryl refers to either an aryl or a heteroaryl group.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 1,2-fluoroethyl, 2-chloroethyl, 2-bromoethyl, 2,2-dichloroethyl, 3-bromopropyl or 2,2,2-trifluoroethyl. The term "fluoroalkyl" as used herein refers to a haloalkyl moiety wherein fluorine is the halogen.

The term "haloalkoxy" as used herein refers to a group —OR where R is haloalkyl as defined herein. The term "haloalkylthio" as used herein refers to a group —SR where R is haloalkyl as defined herein.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "alkoxycarbonyl" and "aryloxycarbonyl" as used herein denotes a group of formula —C(=O)OR wherein R is alkyl or aryl respectively and alkyl and aryl are as defined herein.

The term "cyano" as used herein refers to a carbon linked to a nitrogen by a triple bond, i.e., —C≡N. The term "nitro" as used herein refers to a group —NO$_2$. The term "carboxyl" as used herein refers to a group —CO$_2$H.

The term "acyl" (or "alkanoyl") as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl or "alkanoyl" refers to a group —C(=O)R contain 1 to 6 carbon atoms. The $C_1$ acyl group is the formyl group wherein R=H and a $C_6$ acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The term "cyclic amine" as used herein refers to a saturated carbon ring, containing from 3 to 6 carbon atoms as defined above, and wherein at least one of the carbon atoms is replaced by a heteroatom selected from the group consisting of N, O and S, for example, piperidine, piperazine, morpholine, thiomorpholine, di-oxo-thiomorpholine, pyrrolidine, pyrazoline, imidazolidine, azetidine wherein the cyclic carbon atoms are optionally substituted by one or more substituents, selected from the group consisting of halogen, hydroxy, phenyl, lower alkyl, lower alkoxy or 2-hydrogen atoms on a carbon are both replace by oxo (=O). When the cyclic amine is a piperazine, one nitrogen atom can be optionally substituted by $C_{1-6}$ alkyl, $C_{1-6}$ acyl, $C_{1-6}$ alkylsulfonyl.

The terms "alkylsulfonyl" and "arylsulfonyl" as used herein denotes a group of formula —S(=O)$_2$R wherein R is alkyl or aryl respectively and alkyl and aryl are as defined herein. The term $C_{1-3}$ alkylsulfonylamido as used herein refers to a group RSO$_2$NH— wherein R is a $C_{1-3}$ alkyl group as defined herein. The terms $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl refer to a compound, S(=O)$_2$R wherein R is $C_{1-6}$ haloalkyl, $C_{3-7}$ cycloalkyl, $C_{3-7}$ cycloalkyl-$C_{1-3}$ alkyl and $C_{1-6}$ alkoxy-$C_{1-6}$ alkyl, respectively.

The terms "alkylsulfonylamido" and "arylsulfonylamido" as used herein denotes a group of formula —NR'S(=O)$_2$R wherein R is alkyl or aryl respectively, R' is hydrogen or $C_{1-3}$ alkyl, and alkyl and aryl are as defined herein.

The terms "alkylsulfinyl" and "arylsulfinyl" as used herein denotes a group of formula —S(=O)R wherein R is alkyl or aryl respectively and alkyl and aryl are as defined herein.

The term "acylamino" as used herein denotes a group of formula —NHC(=O)R wherein R is hydrogen or lower alkyl as defined herein. $C_{1-6}$ acyl-amino refers to an acylamino group wherein the C(=O)R moiety contains a total of 6 carbon atoms. The term "$C_{1-3}$ acylamino-$C_{1-6}$ alkyl" refers to a $C_{1-6}$ alkyl substituent wherein one hydrogen atom is replaced by a $C_{1-3}$ acylamino radical.

The term "carbamoyl" as used herein means the radical —CONH$_2$. The prefix "N-alkylcarbamoyl" and "N,N-dialkylcarbamoyl" means a radical CONHR' or CONR'R" respectively wherein the R' and R" groups are independently alkyl as defined herein. The prefix N-arylcarbamoyl" denotes the radical CONHR' wherein R' is an aryl radical as defined herein.

The term "benzyl" as used herein refers to a C₆H₅CH₂ radical wherein the phenyl ring which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamido, arylsulfonylamido, carbamoyl, alkylcarbamoyl and dialkylcarbamoyl, arylcarbamoyl, alkylcarbonylamino, arylcarbonylamino, unless otherwise indicated.

The term "heteroaryl" as used herein without additional definition or limitation refers to "pyridinyl", "pyrazinyl" and "pyridazinyl" rings. The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered nonfused heteroaromatic ring with two nitrogen atoms disposed in a 1,3, a 1,4 and a 1,2 relationship respectively. The respective radical names are in parentheses.

The terms "oxetane" (oxetanyl), "tetrahydrofuran" (tetrahydrofuranyl) and "tetrahydropyran" (tetrahydropyranyl") refer to a four, five and six-membered non-fused heterocyclic ring respectively, each containing one oxygen atom.

The term "aryl" as used herein without further limitation refers to phenyl or naphthyl.

The term "phenylene" as used herein refers to a benzene ring with two open valences. A phenylene moiety has three possible regioisomers, ortho-, -meta- or para-phenylene. Thus the term p-phenylene-(NRᵃNRᵇ) refers to a moiety (i):

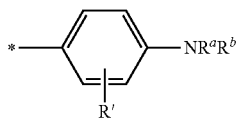

(i)

wherein R' refers to substitution encompassed by the claim.

The terms (i) 3-oxo-3,4-dihydro-pyrazin-2-yl, (ii) 3-oxo-2,3-dihydro-pyridazin-4-yl, and (iii) 2-oxo-1,2-dihydro-pyridin-3-yl refer to the following moieties:

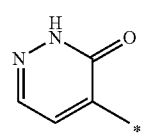

(i)

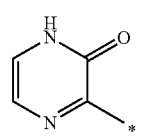

(ii)

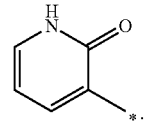

(iii)

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and anti-infective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al.

WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristol Myers Squibb), and ITMN-191 (Intermune).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), MeSO$_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-BuMe$_2$Si (TBDMS), triethylamine (TEA or Et$_3$N), triflate or CF$_3$SO$_2$— (TO, trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), p-toluenesulfonic acid monohydrate (TsOH or pTsOH), 4-Me-C$_6$H4SO$_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system is used herein.

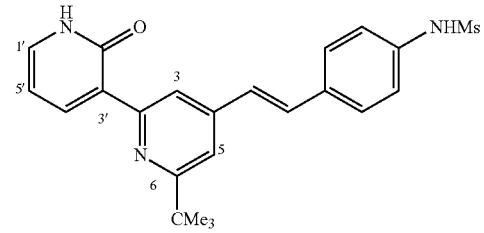

TABLE I

|   | IC$_{50}$[1] (µM) | MS[2] | MP[3] |
|---|---|---|---|
| I-1 (structure) | 0.004 | 424 (ES) | 258.0-260.0 |

TABLE I-continued

| | IC$_{50}$[1] (μM) | MS[2] | MP[3] |
|---|---|---|---|
| I-2 (3-(3-hydroxy-6-tert-butyl-4-(E-4-methanesulfonamidostyryl)pyridin-2-yl)pyridin-2(1H)-one) | 0.177 | 440 (ES) | 178.0–180.0 |
| I-3 (3-(3-hydroxy-6-tert-butyl-4-(2-(4-methanesulfonamidophenyl)ethyl)pyridin-2-yl)pyridin-2(1H)-one) | 0.027 | 442 (ES) | 123.0–125.0 |
| I-4 (methyl 3-cyano-6-tert-butyl-2-(2-oxo-1,2-dihydropyridin-3-yl)isonicotinate) | 5.64 | 312 | 228.0–230.0 |
| I-5 (3-cyano-N-(trans-4-methanesulfonamidocyclohexyl)-6-tert-butyl-2-(2-oxo-1,2-dihydropyridin-3-yl)isonicotinamide) | 0.042 | 472 | 208.0–210.0 |
| I-6 (3-(3-cyano-6-tert-butyl-4-(E-4-methanesulfonamidostyryl)pyridin-2-yl)pyridin-2(1H)-one) | 0.004 | 451 | |
| I-7 (3-(2-tert-butyl-6-(E-4-methanesulfonamidostyryl)pyrimidin-4-yl)pyridin-2(1H)-one) | 0.01 | 425 | 271.0–273.0 |

[1] HCV Polymerase Assay (Example 13)
[2] Parent peak of mass spectra (Electrospray)
[3] Melting Point 2-tert-Butyl-4-cyano-5-hydroxy-pyridine (A-1a) was prepared by the dipolar cyclization of 2-tert-butyl-5-ethoxy-oxazole and acrylonitrile. (S. Bondock, *Heteroatom Chem.* 2005 16(1):49; A. Hassner and B. Fischer, *Heterocycles* 1993 38(2):1441) The requisite oxazole was prepared by dehydration of ethyl (2,2-dimethyl-propionylamino)-acetate (G. Stokker et al., *J. Med. Chem.* 1981 24:115-117). One skilled in the art will appreciate that replacing the tert-butyl ester with other esters will afford pyridines with other C-6 substitution within the scope of the of the present invention.

SCHEME A

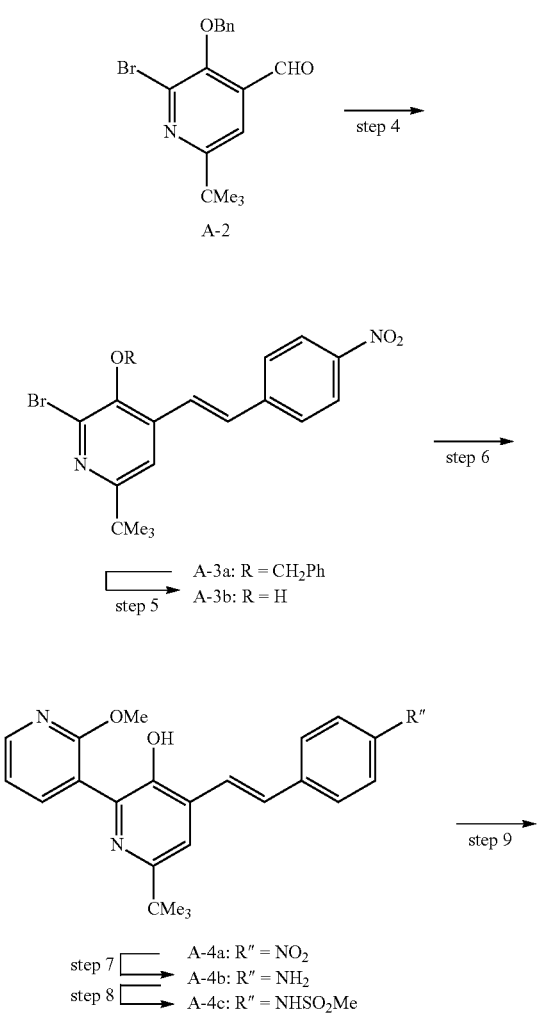

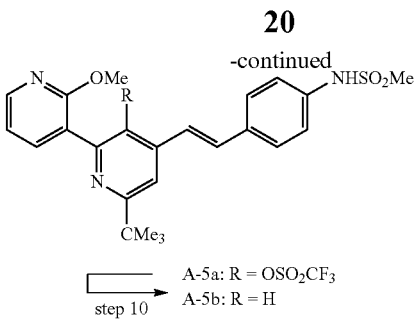

Sequential electrophilic bromination of the pyridine ring of A-1a with NBS and O-alkylation of the hydroxyl affords A-1c. The O-alkylation is conveniently carried out by contacting the phenol with a alkylating agent such as benzyl bromide in the presence of a base. Suitable bases include, but are not limited to, an alkali metal or alkaline metal carbonate or hydroxide, such as $Na_2CO_3$, $K_2CO_3$, $CaCO_3$, $Cs_2CO_3$, NaOH or KOH or an organic amine base such as, pyridine, 2,6-lutidine, collidine, TEA, NMM, DBU or DBN. The reaction is conveniently carried out in an inert solvent such as an ether solvent, e.g., THF, DME or dioxane, an aromatic hydrocarbon solvent, e.g., toluene, or a polar aprotic solvent such as DMF, NMP or DMSO.

To introduce the styryl or phenylethyl substitutent at C-4, the nitrile was reduced to the corresponding aldehyde A-2. Reduction of a nitrile to the corresponding aldehyde can be carried out by reduction with $SnCl_4$ (the Stephen Reduction) or by metal hydride reduction of the nitrile to the imine which in both cases is hydrolyzed to the corresponding aldehyde. Metal hydride reduction can be carried out with $LiAlH_4$, $LiAlH(OEt)_3$ (J. Malek, *Org. Reactions* 1988 36:287-289 and 438-448), DIBAL (A. Fischli, *Helv. Chim. Acta* 1978 61:2560) or $NaAlH_4$. (J. March, *Advanced Organic Chemistry*, John Wiley & Sons: New York, N.Y., 1992, p 918-919).

The styrene side chain is elaborated utilizing a Wittig condensation with a benzylidene-$\lambda^5$-phosphane or a Wadsworth-Horner-Emmons condensation to afford A-3a. The preparation of substituted aryl analogs is readily accomplished utilizing Wittig or HWE reagents prepared by condensation of aryl substituted benzyl halides that can be condensed with triphenylphosphine or triethylphosphite. Diethyl (4-nitrobenzyl)phosphonate is a suitable precursor for some compounds of the present invention substituted with an amine which can, in turn, be optionally sulfonylated.

The Wittig reaction is the reaction of an aldehyde or ketone with a triphenyl phosphonium ylide to afford an alkene and triphenylphosphine oxide. (A. Maercker, *Org. React.* 1965, 14, 270-490; A. W. Carruthers, Some Modern Methods of Organic Synthesis, Cambridge University Press, Cambridge, UK, 1971, pp 81-90) The Wittig reagent is usually prepared from a phosphonium salt, which is in turn prepared by reacting $Ph_3P$ with an alkyl halide. The phosphonium salt is suspended in a solvent such as $Et_2O$ or THF and a strong base such as phenyl lithium or n-butyllithium is added. The Horner-Wadsworth-Emmons reaction (B. E. Maryanoff and A. B. Reitz, *Chem. Rev.* 1989 89:863-927) is the chemical reaction of stabilized phosphonate carbanions with aldehydes (or ketones) to produce predominantly E-alkenes. The Horner-Wadsworth-Emmons reaction (or HWE reaction) is the condensation of stabilized phosphonate carbanions with aldehydes (or ketones) to produce predominantly E-alkenes. In contrast to phosphonium ylides used in the Wittig reaction, phosphonate-stabilized carbanions are more nucleophilic and more basic.

Selective reduction of the nitro group can be carried out with a variety of well-known reducing agents. For example an activated metal such as activated iron, zinc or tin (produced for example by washing iron powder with a dilute acid solution such as dilute hydrochloric acid). Other reagents which have been used to reduce nitro compounds to amines include AlH$_3$—AlCl$_3$, hydrazine and a catalyst, TiCl$_3$, Al—NiCl$_2$-THF, formic acid and Pd/C and sulfides such as NaSH, (NH$_4$)$_2$ S or polysulfides (i.e. the Zinn reaction). Aromatic nitro groups have been reduces with NaBH$_4$ or BH$_3$ in the presence of catalysts such as NiCl$_2$ and CoCl$_2$. (J. March, *Advanced Organic Chemistry*, John Wiley & Sons: New York, N.Y., 1992, p 1216)

Concomitant reduction of the nitro substituent and the olefinic or acetylenic linker is accomplished by catalytic hydrogenation in an inert solvent in the presence of a metal effective to catalyze hydrogenation reactions such as platinum or palladium to afford (4-amino-phenyl)-ethyl derivatives which are HCV polymerase inhibitors or which can be used as intermediates to other compounds of formula I within the scope of the invention Compounds wherein R$^2$ is an ((E)-styryl)-phenyl moiety also be prepared by condensation of substituted toluene derivatives with A-2. This is most practical when toluene is substituted with electronegative groups, such as methyl 2-methyl-5-nitro benzoate, wherein the electronegative groups increase the acidity of protons on the methyl group and allow deprotonation of the methyl and addition to the aldehyde to afford a carbinol that undergoes subsequent dehydration. (see e.g., example 11) On skilled in the art will appreciate that the carboxy group can be produced by hydrolysis. The ester can be further converted to other substituents such an alkoxyalkyl moiety within the scope of the invention by reduction of the ester to afford the benzyl alcohol which can be optionally O-alkylated.

The benzyl protecting group is removed prior to palladium-catalyzed cross coupling of A-3b and 2-methoxy-pyridin-3-yl boronic acid, or a substituted derivative thereof, utilizing Suzuki coupling conditions.

Introduction of the pyridone ring, or related rings can be accomplished by palladium-catalyzed coupling. The Suzuki reaction is a palladium-catalyzed coupling of a boronic acid (R—B(OH)$_2$) wherein R is aryl or vinyl) with an aryl or vinyl halide or triflate (R'Y wherein R'=aryl or vinyl; Y=halide or —OSO$_2$CF$_3$) to afford a compound R-R'. Typical catalysts include Pd(PPh$_3$)$_3$, Pd(OAc)$_2$ and PdCl$_2$(dppf). With PdCl$_2$ (dppf), primary alkyl borane compounds can be coupled to aryl or vinyl halide or triflate without β-elimination. Highly active catalysts have been identified (see, e.g. J. P. Wolfe et al., *J. Am. Chem. Soc.* 1999 121(41):9550-9561 and A. F. Littke et al., *J. Am. Chem. Soc.* 2000 122(17):4020-4028). The reaction can be carried out in a variety of organic solvents including toluene, THF, dioxane, 1,2-dichloroethane, DMF, DMSO and acetonitrile, aqueous solvents and under biphasic conditions. Reactions are typically run from about room temperature to about 150° C. Additives (e.g. CsF, KF, TlOH, NaOEt and KOH) frequently accelerate the coupling. There are a large number of parameters in the Suzuki reaction including the palladium source, ligand, additives and temperature and optimum conditions sometimes require optimization of the parameters for a given pair of reactants. A. F. Littke et al., supra, disclose conditions for Suzuki cross-coupling with arylboronic acids in high yield at RT utilizing Pd$_2$(dba)$_3$/P (tert-Bu)$_3$ and conditions for cross-coupling of aryl- and vinyl triflates utilizing Pd(OAc)$_2$/P(C$_6$H$_{11}$)$_3$ at RT. J. P. Wolf et al., supra, disclose efficient condition for Suzuki cross-coupling utilizing Pd(OAc)$_2$/o-(di-tert-butylphosphino)biphenyl or o-(dicyclohexylyphosphino)biphenyl. One skilled in the art can determine optimal conditions without undue experimentation.

Sulfonylation of the resulting amine is typically achieved by condensing the amine with a sulfonylating agent, typically a sulfonyl chloride, in the presence of a base such as TEA or pyridine.

When C-3-deoxy compounds within the scope of the invention are sought, the phenol A-4c can be reduced to the corresponding arene by sulfonylating the phenol and reducing the resulting aryl-, alkyl- or fluoroalkyl-sulfonyloxy substituent with palladium and a proton source. Aryl triflates undergo oxidative addition to Pd(0) complexes which undergo protonation to form the arene in the presence of triethylammonium formate. G. A. Peterson et al. (*Tetrahedron Lett.* 1987 13:1381) reported similar results and also carried out the reaction using NaBH$_4$ as the hydrogen donor. S. Cacchi et al. (*Tetrahedron Lett.* 1986 27:5541) effectively deoxygenated triflate esters of phenols with Pd(OAc)$_2$ and Pd(PPh$_3$)$_4$ in TEA, HCO$_2$H and DMF heated to 60° C. B. Lipshutz et al. (*Tetrahedron Lett.*, 1999 40:6871) reported similar reductions using amine-borane complexes as the hydrogen donor in the presence of Pd(PPh$_3$)$_4$, K$_2$CO$_3$ and MeCN. W. Cabri et al. (*J. Org. Chem.* 1990 55:350) were able to deoxygenate mesylate esters with Pd(OAc)$_2$ and biphosphine ligands such as 1,1'-bis(diphenylphosphine)ferrocene (dppf) under similar condition at 90° C.

Dealkylation of the O-methyl ether to afford the pyridone can be effected with HBr and HOAc at elevated temperatures to afford the desired pyridine. Alternatively a 2-benzyloxy-pyridin-3-yl boronic acid can be used which can be debenzylated either with HBr/HOAc or by hydrogenolysis.

Compounds within the scope of the present claims wherein the hydroxyl group at C-3 is retained in the final compound can be prepared by elaboration of the styryl side chain as described above followed by reduction of the nitro group and sulfonylation of the aryl amine whilst the benzyloxy group remains in place. Cleavage of the O-methyl ether and subsequent controlled hydrogenation allows selective debenezylation of the benzyl ether. One skilled in the art will readily appreciate that routine optimization will identify reaction conditions which are selective debenzylation or which are more vigorous and allow debenzylation and concomitant reduction of the styryl double bond.

Compounds encompassed by the present invention wherein C-4 is substituted by a carboxyamido moiety are prepared by condensation of a suitably substituted carboxylic acid and an amine. When C-3 is substituted by a cyano group were prepared from ethyl 6-tert-butyl-2-chloro-3-cyano-isonicotinoate (26). After introduction of the latent pyridone by palladium catalyzed coupling as described previously the amide is formed by acylation of the amine which can be effected by preparing an activated carboxylic acid such as an acid chloride or a symmetrical or mixed acid anhydride and reacting the activated derivative with an amine in an inert solvent such as DMF, DCM, THF, with or without water as a co-solvent, at temperatures between 0° and 60° C. generally in the presence of a base such as Na$_2$CO$_3$, NaHCO$_3$, K$_2$CO$_3$, DIPEA, TEA or pyridine and the like to afford an amide. Carboxylic acids are converted into their acid chlorides using standard reagents well known to someone skilled in the art, such as thionyl chloride, oxalyl chloride, phosphoryl chloride and the like. Those reagents can be used in presence of bases such as DIPEA, TEA or pyridine.

Alternatively a carboxylic acid can be converted in situ into activated acids by different peptide coupling procedures known to those skilled in the art. These activated acids were reacted directly with the amines to afford amides. Said activation with those peptide coupling procedures can involve the use of an activating agent like EDCI, DCC, benzotriazol-1-yloxy-tris(dimethylamino)phosphonium hexafluorophosphate (BOP), bromo-tris-pyrrolidinophosphonium hexafluorophosphate (PyBrOP), or 2-fluoro-1-methylpyridinium p-toluenesulphonate (Mukaiyama's reagent) and the like, optionally in the presence of modifiers such as HOBt, with or without a base such NMM, TEA or DIPEA in an inert solvent such as DMF or DCM at temperatures between 0° C. and 60° C. The reaction may alternatively be carried out in presence of O-(7-azabenzotriazol-1-yl)-N,N,N',N'-tetramethyluronium hexafluorophosphate (HATU) or 1-hydroxy-7-azabenzotriazole (HOAt) and TEA or DIPEA in DMF, DCM or THF. Acylation of amines (J. March, supra pp. 417-425; H. G. Benz, *Synthesis of Amides and Related Compounds* in *Comprehensive Organic Synthesis*, E. Winterfeldt, ed., vol. 6, Pergamon Press, Oxford 1991 pp. 381-411; see R. C. Larock, *Comprehensive Organic Transformations-A Guide to Functional Group Preparations,* 1989, VCH Publishers Inc., New York; pp. 972-976) has been reviewed.

Compounds within the scope of the present invention wherein the central ring is a pyrimidine can be prepared from a 2-alkyl-4,6-dichloro-pyrimidine such as 4,6-dichloro-2-(1,1-dimethylethyl)-pyrimidine (CASRN 1044771-51-8) by sequential palladium catalyzed coupling of N-{4-[(E)-2-(4,4,6-trimethyl-[1,3,2]dioxaborinan-2-yl)-vinyl]-phenyl}-methanesulfonamide (39) and 2-oxo-1,2-dihydropyridine-3-boronic acid (CASRN 951655-49-5) to introduce the side chains. One skilled in the art will appreciate that Suzuki coupling 39 can be used advantageously in the pyridine series in place of the Wittig reaction when 4-halopyridine derivatives are available.

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 8. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-{4-[(E)-2-(6-tert-Butyl-3-hydroxy-2'-oxo-1',2'-dihydro-[2,3']bipyridinyl-4-yl)-vinyl]-phenyl}-methanesulfonamide (I-1) (SCHEME A)

step 1—N-Bromosuccinamide (196 mg, 1.1 mmol) was added to a solution of the A-1a (176 mg, 1 mmol, CASRN 69213-44-1) in DMF (3 mL). After stirring at RT for 30 min, the reaction was poured into sat'd. aq. NH$_4$Cl and EtOAc. The organic phase was separated, dried (MgSO$_4$), filtered and evaporated and the residue containing A-1b was used without additional purification.

step 2—The residue from step 1 was dissolved in DMF (3 mL) and treated with K$_2$CO$_3$ (276 mg, 2 mmol) and benzyl bromide (0.13 mL, 2 mmol). After stirring at RT overnight, the reaction was partitioned between with brine and EtOAc. The crude residue was purified by SiO$_2$ chromatography eluting with 9:1 hexanes/EtOAc to afford 124 mg (36%) of A-1c.

step 3—To a solution of A-1c (120 mg, 0.35 mmol) cooled to 0° C. was added DIBAL-H (0.53 mL, 0.53 mmol). After stirring at 0° C. for 10 min, the reaction was diluted with EtOAc and aq. 2N HCl. The organic phase was separated, dried (MgSO$_4$), filtered and evaporated. The crude residue was purified by SiO$_2$ chromatography eluting with 95:5 hexanes/EtOAc to afford 85 mg (70%) of A-2.

step 4—To a slurry of NaH (24 mg, 0.6 mmol, 60% in mineral oil dispersion) and 15-crown-5 (44 mg, 0.2 mmol) in THF (1 mL) cooled to 0° C. was added a solution of diethyl (4-nitro-phenyl)-phosphonate (273 mg, 1 mmol) in THF (1 mL). After stirring at 0° C. for 10 min, a solution of A-2 (173 mg, 0.641 mmol) in THF (1 mL) was added dropwise. The reaction was stirred at RT for 1 h. The reaction mixture is partitioned between aq 1N HCl and EtOAc. The organic phase was separated, dried (MgSO$_4$), filtered and evaporated. The crude residue was purified by SiO$_2$ chromatography eluting with 95:5 hexanes/EtOAc to afford 221 mg (95%) of A-3a.

step 5—To a solution of A-3a (150 mg, 0.32 mmol) in HOAc (1 mL) in a 5 mL microwave vial was added dropwise 48% aq. HBr (0.022 mL), sealed and heated at 60° C. overnight. The solution was cooled and partitioned between sat'd. aq. NaHCO$_3$ and EtOAc. The organic layer was separated, dried (MgSO$_4$), filtered and concentrated. The crude residue was purified by SiO$_2$ chromatography eluting with 95:5 hexanes/EtOAc to afford 70 mg (58%) of A-3b.

step 6—A sealed tube containing A-3b (70 mg, 0.19 mmol), 2-methoxy-pyridin-3-yl boronic acid (21, 37 mg, 0.24 mmol), Pd(PPh$_3$)$_4$ (22 mg, 0.019 mmol) and Na$_2$CO$_3$ (60 mg, 0.57 mmol) in a mixture of MeOH (1 mL) and DCM (0.3 mL) was irradiated in a microwave reactor at 120° C. for 40 min. The reaction mixture was cooled to RT and diluted with EtOAc. The organic layer was washed with water, dried (MgSO$_4$), filtered and concentrated. The crude residue was purified by SiO$_2$ chromatography eluting with 15:85 EtOAc/hexane gradient to afford 55 mg (74%) of A-4a.

step 7—Tin chloride dihydrate (108 mg, 0.48 mmol) was added to a solution of the A-4a (47 mg, 0.1 mmol) in EtOAc (3 mL) and the mixture heated at reflux for 2 h. The reaction was cooled to RT and poured into ice cold sat'd. aq. NaHCO$_3$. The slurry was extracted with EtOAc. The organic layer was separated, dried (MgSO$_4$), filtered and concentrated. The crude residue was purified by SiO$_2$ chromatography to afford A-4-b.

step 8—Methanesulfonyl chloride (31.9 µL, 0.41 mmol) was added to a solution of A-4-b (160 mg, 0.41 mmol) in pyridine (2 mL) at 0° C. After stirring at 0° C. for 10 min, the reaction was poured into sat'd. aq. NH$_4$Cl and extracted with EtOAc. The organic layer was separated, dried (MgSO$_4$), filtered and concentrated. The crude residue was purified by SiO$_2$ chromatography to afford 64 mg (39%) of A-4c.

step 9—Triflic anhydride (26.1 µL, 0.16 mmol) and Na$_2$CO$_3$ (30 mg, 0.28 mmol) were added to a solution of A-4c (64 mg, 0.14 mmol) in DCM (2 mL). After stirring at RT for 3 h, the reaction was treated with sat'd. aq. NH$_4$Cl and EtOAc. The organic layer was separated, dried (MgSO$_4$), filtered and concentrated. The crude residue was purified by SiO$_2$ chromatography eluting with 7:3 hexanes/EtOAc to afford 58 mg (71%) of A-5a.

step 10—A tube was charged with A-5a (58 mg, 0.1 mmol), Pd(OAc)$_2$ (1.1 mg, 0.005 mmol) and diphenylphosphinoferrocene (2.8 mg, 0.005 mmol). The tube was purged with argon and charged sequentially with DMF (1 mL) and TEA (41.8 µL, 0.3 mmol) and formic acid (8 µL, 0.2 mmol). The tube was sealed and heated up at 80° C. for 3 h. The reaction was treated with sat'd. aq. NH$_4$Cl and EtOAc. The organic layer was separated, dried (MgSO$_4$), filtered and concentrated. The crude residue was purified by SiO$_2$ chromatography eluting with 65:35 hexanes/EtOAc to afford 34 mg (79%) of A-5b.

step 11—To a solution of A-5b (47 mg, 0.11 mmol) in HOAc (1 mL) in a microwave vial was added dropwise 48% aq. HBr (0.065 mL). The tube was sealed and heated at 60° C. After 20 min a solid precipitated and the reaction was treated with sat'd. aq. NaHCO$_3$ and EtOAc. The organic layer was separated, dried (MgSO$_4$), filtered and concentrated. The crude residue was purified by SiO$_2$ chromatography eluting with 15:85 hexanes/EtOAc to afford I-1.

N-(4-{(E)-2-[3-tert-Butyl-5-(5-fluoro-2-oxo-1,2-dihydro-pyridin-3-yl)-phenyl]-vinyl}-phenyl)-methanesulfonamide is prepared analogously except in step 6, 21 is replaced with 5-fluoro-2-methoxy-pyridin-3-yl boronic acid (CASRN 957120-32-0).

N-(4-{(E)-2-[3-tert-Butyl-5-(6-methoxy-2-oxo-1,2-dihydro-pyridin-3-yl)-phenyl]-vinyl}-phenyl)-methanesulfonamide is prepared analogously except in step 6, 21 is replaced with 2,6-di-methoxy-pyridin-3-ylboronic acid (CASRN 221006-70-8).

N-(4-{(E)-2-[3-tert-Butyl-5-(6-methyl-2-oxo-1,2-dihydro-pyridin-3-yl)-phenyl]-vinyl}-phenyl)-methanesulfonamide is prepared analogously except in step 6, 21 is replaced with 6-methyl-2-methoxy-pyridin-3-yl boronic acid (CASRN 1000802-75-4).

Example 2

N-{4-[(E)-2-(6-tert-Butyl-3-hydroxy-2'-oxo-1',2'-dihydro-[2,3']bipyridinyl-4-yl)-vinyl]-phenyl}-methanesulfonamide (I-2)

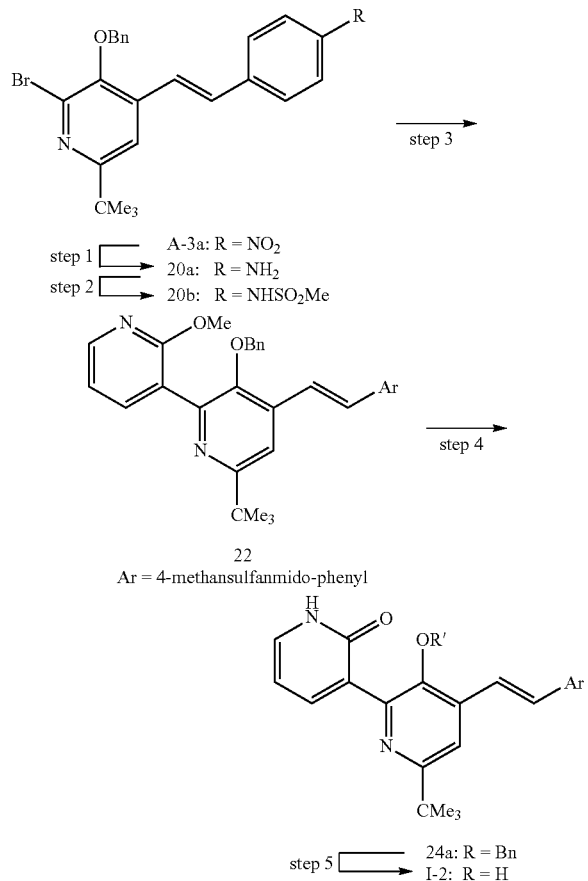

Reduction of the nitro group (step 1) and sulfonylation of the resulting amine (step 2) were carried out in accord with the procedures described in steps 7 and 8 of example 1 to afford 20b. Both intermediates were purified by $SiO_2$ chromatography.

step 3—A tube was charged with 20b (90 mg, 0.18 mmol), 21 (32 mg, 0.22 mmol), $Pd(PPh_3)_4$ (21 mg, 0.018 mmol), $Na_2CO_3$ (57 mg, 0.54 mmol) and a mixture of MeOH (0.3 mL) and DCM (0.9 mL), sealed and irradiated in a microwave reactor at 115° C. for 35 min. The reaction mixture was cooled to RT and diluted with EtOAc. The organic layer was washed with water, dried ($MgSO_4$), filtered and concentrated. The crude residue was purified by $SiO_2$ chromatography eluting with 40:60 EtOAc/hexane to afford to afford 88 mg (90%) of 22.

step 4—To a solution of 22 (300 mg, 0.55 mmol) in HOAc (4 mL) in a vial was added dropwise 48% aq. HBr (0.18 mL, 1.65 mmol). The tube was sealed and reaction mixture was heated at 60° C. overnight. The reaction was treated with aq. $NaHCO_3$ and EtOAc. The organic layer was separated, dried ($MgSO_4$), filtered and concentrated to afford 220 mg (76%) of 24a that was used in the next step without additional purification.

step 5—Palladium (10% wt. on carbon, 10 mg) was added to a solution of 24a (100 mg, 0.19 mmol) in MeOH (5 mL) at RT. The reaction was stirred under 1 atm of $H_2$ for 2 h. The catalyst was filtered and the filtrate was concentrated. The crude product was purified on a preparative $SiO_2$ TLC plate developed with 30:70 hexanes/EtOAc to afford I-2.

Example 3

N-{4-[2-(6-tert-Butyl-3-hydroxy-2'-oxo-1',2'-dihydro-[2,3']bipyridinyl-4-yl)-ethyl]-phenyl}-methanesulfonamide (I-3)

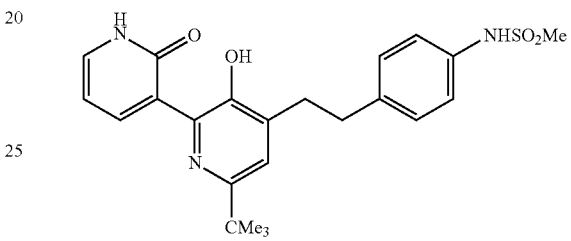

Palladium (20% wt. on carbon, 48 mg) was added to a solution of 24a (120 mg, 0.23 mmol) in 1:1 EtOAc/MeOH (8 mL) at RT. The reaction was stirred under 1 atm of $H_2$ overnight. The catalyst was filtered and the filtrate was concentrated in vacuo. The crude product was purified on a preparative $SiO_2$ TLC plate developed with 30:70 hexanes/EtOAc to afford I-3.

Example 4

6-tert-Butyl-3-cyano-2'-oxo-1',2'-dihydro-[2,3']bipyridinyl-4-carboxylic acid methyl ester (I-4)

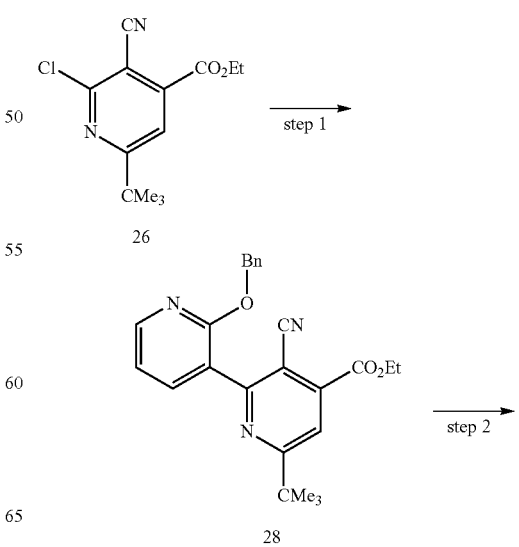

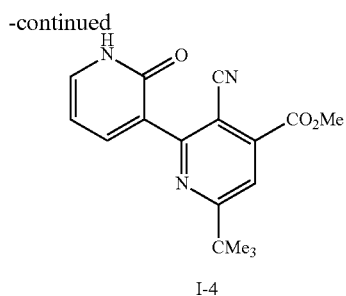

I-4 step 1—A sealed microwave tube was charged with 26 (1.00 g, 3.75 mmol, CASRN 175204-47-7), 2-benzyloxy-pyridin-3-yl boronic acid (1.12 g, 4.87 mmol, CASRN 072952-41-0), $Na_2CO_3$ (596 mg, 5.62 mmol) and Pd(dppf)$Cl_2 \cdot CH_2Cl_2$ (153 mg, 0.187 mmol) and a mixture of MeOH (8.0 mL), DCM (0.5 mL) and $H_2O$ (0.5 mL), sealed and irradiated in a microwave synthesizer at 110° C. for 30 min. The reaction mixture was diluted with DCM, filtered through a pad of CELITE, and the filtrate was concentrated. The crude residue was purified by $SiO_2$ chromatography eluting with a EtOAc/hexane gradient (5 to 30% EtOAc in hexanes) to afford 1.49 g of 28 as a white solid.

step 2—A suspension of 28 (87 mg, 0.22 mmol) and Pd(OH)$_2$/C (50 mg) in EtOAc (20 mL) at RT was stirred under 1 atmosphere of $H_2$ for 1.5 h. The catalyst was filtered off, and the filtrate was concentrated. The crude product was recrystallized from EtOAc to afford 59 mg of I-4 as a white solid.

Example 5

6-tert-Butyl-3-cyano-2'-oxo-1',2'-dihydro-[2,3']bipyridinyl-4-carboxylic acid (4-methanesulfonylaminocyclohexyl)-amide (I-5)

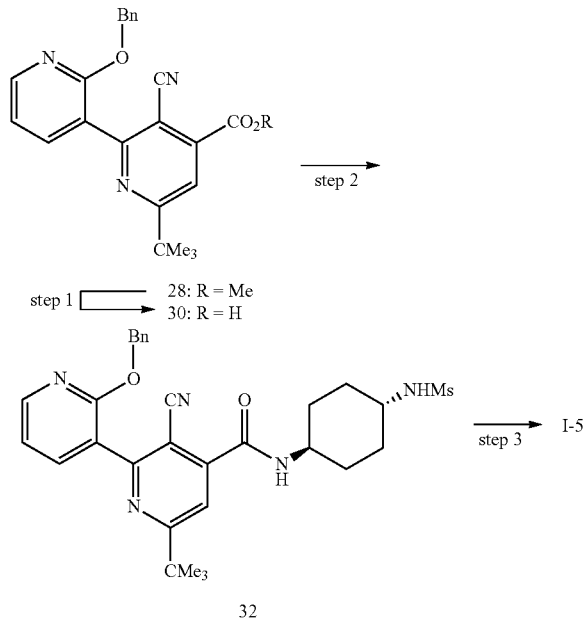

step 1—A solution of 28 (527 mg, 1.31 mmol) and 1N aq. LiOH (2.50 mL) in a mixture of THF (8 mL), MeOH (2 mL) and $H_2O$ (4 mL) was stirred at RT for 1 h. The reaction was acidified to pH of ca. 6.5 with 1N aq. HCl then the organic volatiles were removed under reduced pressure. The residue was partitioned between EtOAc and $H_2O$. The organic layer was separated, dried (MgSO$_4$) and concentrated to give 500 mg of 30 which was used in the next step without further purification.

step 2—To a solution of 30 (139 mg, 0.36 mmol) and trans-N-(4-amino-cyclohexyl)-methanesulfonamide (90 mg, 0.468 mmol, CASRN 264608-37-9) in DMF at 0° C. was sequentially added HOBt (63 mg, 0.468 mmol) and EDCI (90 mg, 0.468 mmol). The resulting mixture was stirred from 0° C. and allowed to warm to RT over 16 h. The reaction was then diluted with 1N aq. HCl and extracted with EtOAc. The organic layer was washed with $H_2O$, brine, dried (MgSO$_4$) and concentrated. The crude residue was purified by $SiO_2$ chromatography eluting with a EtOAc/hexane gradient (50 to 100% EtOAc) to afford 115 mg of 32 as a foam.

step 3—A suspension of 32 (105 mg, 0.19 mmol) and Pd(OH)$_2$/C (35 mg) in EtOAc (10 mL) and MeOH (2 mL) was stirred at RT under 1 atmosphere of $H_2$ for 1.5 h. The catalyst was filtered off, and the filtrate was concentrated to give 78 mg of I-5 as a solid.

N-{1-[3-tert-Butyl-5-(2-oxo-1,2-dihydro-pyridin-3-yl)-benzoyl]-pyrrolidin-3-yl}-methanesulfonamide is prepared analogously except in step 2, trans-N-(4-amino-cyclohexyl)-methanesulfonamide is replaced with 33.

N-pyrrolidin-3-ylmethyl-methanesulfonamide (33)

TEA (1.05 mL, 7.5 mmol) was added to a solution of (R)-3-(aminomethyl)-1-N-Boc-pyrrolidine (1 g, 5 mmol) in DCM (25 mL) at 0° C. Methanesulfonyl chloride (0.43 mL, 5.5 mmol) was then added. After stirring at 0° C. for 2 h, the reaction mixture was diluted with water. The organic phase was separated, dried (MgSO$_4$), filtered and concentrated. The crude material was treated with 1M HCl in MeOH (25 mL) at RT and stirred at RT for 20 h. The volatiles were removed under reduced pressure to 0.95 g of 33 as a white solid.

N-{4-[3-tert-Butyl-5-(2-oxo-1,2-dihydro-pyridin-3-yl)-benzoyl]-morpholin-2-ylmethyl}-methanesulfonamide is prepared analogously except in step 2, trans-N-(4-amino-cyclohexyl)-methanesulfonamide is replaced with N-morpholin-2-ylmethyl-methanesulfonamide (CASRN 1153762-77-6). The latter can be readily prepared by analogous procedures from tert-butyl 2-aminomethylmorpholine-4-carboxylate (CASRN 140645-53-0)

Example 6

N-{4-[2-(6-tert-Butyl-3-cyano-2'-oxo-1',2'-dihydro-[2,3']bipyridinyl-4-yl)-ethyl]-phenyl}-methanesulfonamide (I-6)

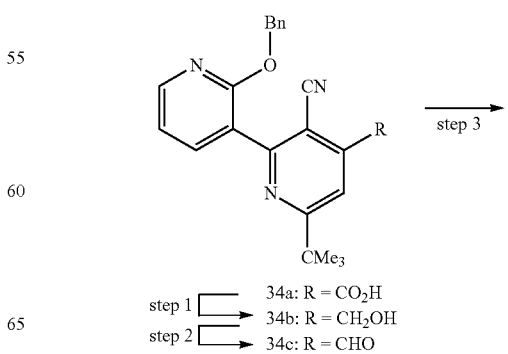

step 1 → 34a: R = CO$_2$H
       → 34b: R = CH$_2$OH
step 2 → 34c: R = CHO

-continued

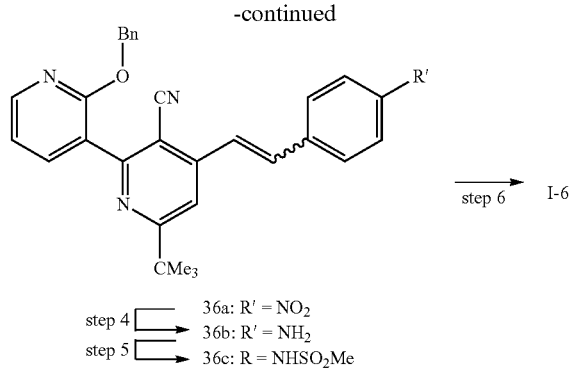

step 4 ⎡ 36a: R' = NO₂
      ⎣ 36b: R' = NH₂
step 5 ⎣ 36c: R = NHSO₂Me step 1—To a solution of 34a (180 mg, 0.46 mmol) in THF (6 mL) RT was added sequentially BOP (247 mg, 0.56 mmol) and i-Pr₂NEt (97 μL, 0.56 mmol). The mixture was stirred at RT for 10 min before NaBH₄ (21 mg, 0.56 mmol) was added. The resulting mixture was stirred for 1 h then concentrated in vacuo. The residue was re-dissolved in EtOAc and washed with 1N aq. HCl, sat'd. aq. NaHCO₃, brine, dried (MgSO₄) and concentrated. The crude residue was purified by SiO₂ chromatography eluting with an EtOAc/hexane gradient (10 to 40% EtOAc) to afford 109 mg of 34b as a syrup.

step 2—To a solution of 34b (140 mg, 0.37 mmol) in DCM (8 mL) cooled to 0° C. was added NaHCO₃ (63 mg, 0.75 mmol) and followed by Dess-Martin periodinane (239 mg, 0.56 mmol). The mixture was stirred at 0° C. for 1 h. The reaction was concentrated under reduced pressure. The crude residue was purified by SiO₂ chromatography eluting with an EtOAc/hexane gradient (10 to 20% EtOAc) to afford 137 mg of 34c.

step 3—To a solution of diethyl (4-nitrobenzyl)phosphonate (132 mg, 0.48 mmol) in THF (5 mL) at 0° C. was added dropwise a solution of 1M NaHMDS (485 μL, 0.48 mmol) in THF. The mixture was stirred at 0° C. for 15 min then a solution of 34c (100 mg, 0.27 mmol) in THF (4 mL) was added. The resulting mixture was stirred from 0° C. to RT over 5 h before it was quenched with sat'd. aq. NH₄Cl. The reaction mixture was extracted with EtOAc. The organic extract was washed with H₂O, brine, dried (MgSO₄) and concentrated. The crude residue was purified by SiO₂ chromatography eluting with an EtOAc/hexane gradient (10 to 50% EtOAc) to afford 78 mg of 36a as a mixture of E,Z-isomers.

step 4—A solution of 36a (76 mg, 0.15 mmol) and SnCl₂.H₂O (174 mg, 0.77 mmol) in a mixture of DMF (4 mL) and EtOH (4 mL) was heated at 40° C. for 1 day. The reaction was allowed to cool to RT, poured into a mixture of sat'd. aq. NaHCO₃ and DCM, and filtered. The filtrate was concentrated and the residue was partitioned between EtOAc and H₂O. The organic layer was washed with brine, dried (MgSO₄) and concentrated. The crude residue was purified by SiO₂ chromatography eluting with an EtOAc/hexane gradient (30% EtOAc) to afford 48 mg of 36b as a mixture of E,Z-isomers.

step 5—Sulfonylation of 36b was carried out in accord with the procedure in step 8 of example 1. The crude product was purified on a preparative SiO₂ TLC plate developed with 50% EtOAc/hexane to afford 36c as a mixture E,Z-isomers.

step 6—A mixture of 36c (33 mg, 0.069 mmol) and Pd(OH)₂/C (30 mg) in EtOAc (20 mL) at RT was stirred under 1 atmosphere of H₂ for 2 h before the catalyst was filtered off. The filtrate was concentrated. The crude residue was purified on a preparative SiO₂ TLC plate developed with EtOAc. The product was slightly impure and further purified by preparative HPLC to afford 3.7 mg of I-6 as a white solid.

Example 7

N-(4-{(E)-2-[2-tert-Butyl-6-(2-oxo-1,2-dihydro-pyridin-3-yl)-pyrimidin-4-yl]-vinyl}-phenyl)-methanesulfonamide (I-7)

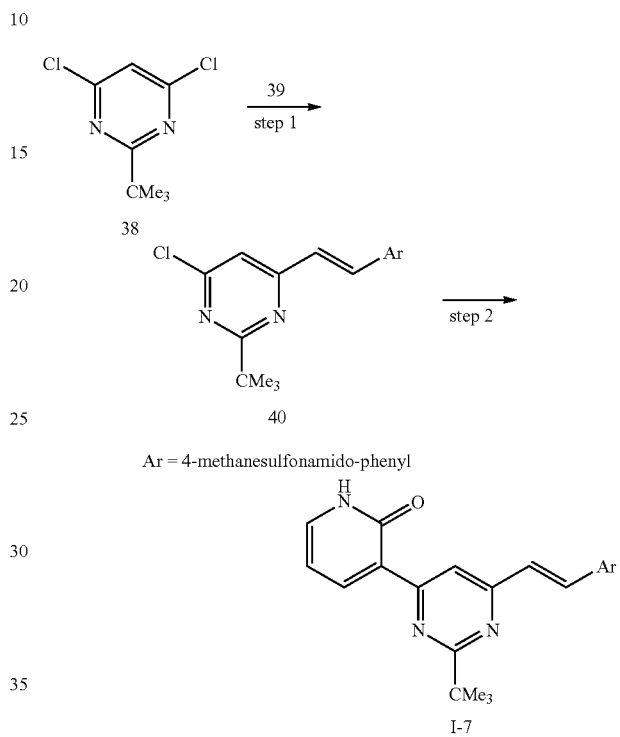

Ar = 4-methanesulfonamido-phenyl

N-{4-[(E)-2-(4,4,6-Trimethyl-[1,3,2]dioxaborinan-2-yl)-vinyl]-phenyl}-methanesulfonamide (39)—To a solution of Pd(OAc)₂ (0.076 g), tris-(ortho-tolyl)-phosphine (0.246 g, 1 mmol) and toluene (16 mL) were added sequentially N-(4-iodo-phenyl)-methanesulfonamide (2.00 g, 7 mmol, CASRN 102294-59-7), tributyl amine (1.92 mL) and 4,4,6-trimethyl-2-vinyl-[1,3,2]dioxaborinane (1.244 g, 8 mmol, CASRN 4627-10-5). The reaction was heated at reflux for 72 h, cooled to RT and partitioned between Et₂O (100 mL) and 1M HCl (20 mL). The aqueous layer was withdrawn and re-extracted with Et₂O. The organic phases were washed sequentially with H₂O and brine. The extracts were combined, dried (Na₂SO₄), filtered and evaporated. The residue was purified by SiO₂ chromatography eluting with an EtOAc/hexane gradient (0 to 30% EtOAc) to afford 1.4 g (58%) of 39.

step 1: A tube was charged with 38 (0.13 g, 0.62 mmol, CASRN 1044771-51-8), 39 (0.20 g, 0.62 mmol), Pd(PPh₃)₄ (0.036 g, 0.030 mmol) and K₃PO₄.H₂O (0.43 g, 1.9 mmol) in DMF (2.5 mL), sealed and heated to 100° C. for 6 h with stirring. The reaction mixture was diluted with toluene, washed with water, dried (Na₂SO₄), filtered, and concentrated under reduced pressure. The crude residue so obtained was purified by SiO₂ chromatography eluting with EtOAc/hexane to afford 0.095 g (41%) of 40.

step 2—A mixture of 40 (0.090 g, 0.25 mmol), 2-oxo-1,2-dihydropyridine-3-boronic acid (0.041 g, 0.30 mmol, CASRN 951655-49-5), Pd(PPh₃)₄ (0.028 g, 0.025 mmol) and Na₂CO₃ (0.078 g, 0.74 mmol) in DCM-MeOH (4:1, 3 mL) was irradiated in a microwave synthesizer at 115° C. for 30 min. The reaction mixture was partitioned between DCM and water and the organic phase dried (Na$_2$SO$_4$), filtered and concentrated under reduced pressure. The crude residue was purified by SiO$_2$ chromatography eluting with EtOAc/HOAc, followed by trituration (DCM/MeOH) to afford 0.016 g (15%) of 1-7.

Example 8

N-(4-{(E)-2-[3-tert-Butyl-5-(2,4-dioxo-1,2,3,4-tetrahydro-pyrimidin-5-yl)-phenyl]-vinyl}-phenyl)-methanesulfonamide (42)

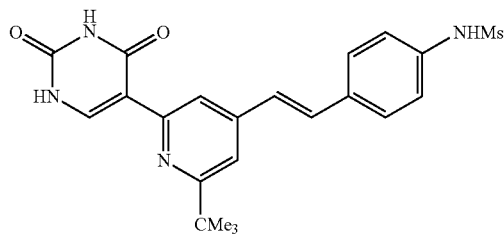

The title compound is prepared in accord with the procedure in example 1, except in step 6 of example 1, 21 is replaced with 2,4-dioxo-1,2,3,4-tetrahydro-pyrimidin-5-yl boronic acid (CASRN 70523-22-7).

Example 9

N-(4-{(E)-2-[3-tert-Butyl-5-(3-oxo-2,3-dihydro-pyridazin-4-yl)-phenyl]-vinyl}-phenyl)-methanesulfonamide (44)

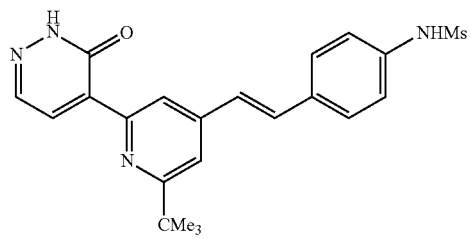

The title compound is prepared in accord with the procedure in example 1, except in step 6 of example 1, 21 is replaced 45.

B-(2,3-dihydro-3-oxo-4-pyridazinyl)-boronic acid (45)

step a—A 1 L round-bottom flask was charged with 4-chloro-5-hydrazinyl-3(2H)-pyridazinone (8.0 g, 50 mmol, CASRN 6959-56-4), CuSO$_4$.5H$_2$O (26.12 g, 10.5 mmol) and H$_2$O (300 mL) and the mixture was stirred and heated at reflux overnight. The reaction was cooled to 0° C. and an aq. solution of NaOH was added until the pH was 4. The aqueous layer was thrice extracted with EtOAc (500 mL each). The combined extracts were dried (Na$_2$SO$_4$), filtered and evaporated. The remaining aqueous phase was adjusted to pH of 2 with 37% HCl and the solution extracted six times with EtOAc. The extracts were combined, dried (Na$_2$SO$_4$), filtered and evaporated to afford 4.75 g of 4-chloro-2H-pyridazin-3-one (46)

step b—A microwave vial was charged with 74 (0.400 g, 3 mmol), bis-(pinacolato)diboron (0.934 g, 4 mmol), dicyclohexyl[2',4',6'-tris(1-methylethyl)[1,1'-biphenyl]-2-yl]-phosphine (X-Phos, 0.058 g, 0.12 mmol), Pd$_2$(dba)$_3$ (0.056 g, 0.061 mmol) and KOAc (0.902 g, 9 mmol) and the flask was evacuated and back-filled with Ar and sealed. Dioxane (6 mL) was added and the reaction heated at 110° C. overnight. The reaction mixture was cooled to RT and extracted with EtOAc (120 mL). The organic extract was washed sequentially with H$_2$O (10 mL) and brine (10 mL), dried (Na$_2$SO$_4$), filtered and evaporated. The crude product was triturated with Et$_2$O to afford 0.217 g of 45.

Example 10

N-(4-{(E)-2-[6-tert-Butyl-3-hydroxy-6'-(2-hydroxy-ethoxymethyl)-2'-oxo-1',2'-dihydro-[2,3']bipyridinyl-4-yl]-vinyl}-phenyl)-methanesulfonamide (54)

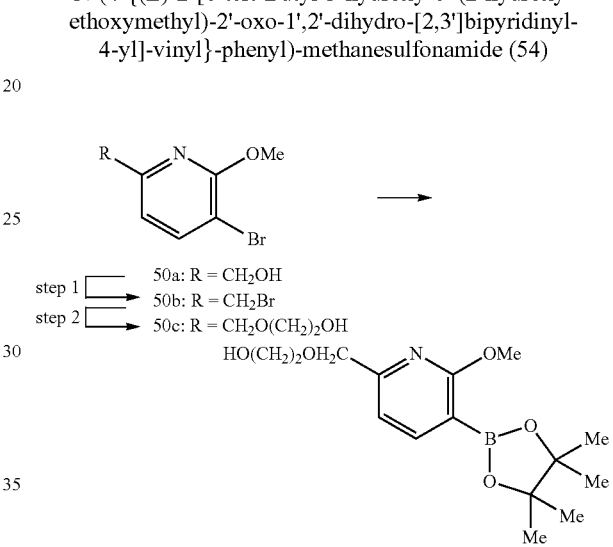

(5-Bromo-6-methoxy-pyridin-2-yl)-methanol (50a)

step a—To a solution of 3-bromo-2-chloro-6-methyl-pyridine (2.0 g, 0.687 mmol) in CHCl$_3$ was added MCPBA (3.3 g, 19.1 mmol) and the resulting solution was heated at 50° C. overnight, The resulted solution was cooled and partitioned between DCM and sat'd. aq. NaHCO$_3$. The organic layer was dried (Na$_2$SO$_4$), filtered and concentrated in vacuo. The crude product was purified by SiO$_2$ chromatography eluting with an EtOAc/hexane gradient (30 to 80% EtOAc) to afford 1.88 g (87%) of 3-bromo-2-chloro-6-methyl-pyridine 1-oxide (52a) as a white solid.

step b—A solution of 52a (0.5 g) and 0.5 M NaOMe/MeOH (4.9 mL) was stirred at RT overnight. The reaction mixture was concentrated in vacuo and the residue loaded on a SiO$_2$ column and eluted with 5% MeOH/DCM to afford 3-bromo-2-methoxy-6-methyl-pyridine 1-oxide (52b).

step c—A solution of 52b (0.47 g) and acetic anhydride (4.0 mL) was heated at 120° C. for 2 h, The reaction mixture was concentrated in vacuo and purified on a SiO$_2$ column eluting with 5% EtOAc/hexane to afford methyl 5-bromo-6-methoxy-pyridin-2-yl-acetate (52c).

step d—A solution of 52c (0.060 g), 5% aq. NaHCO$_3$ (2 mL) and MeOH (2 mL) was heated at reflux for 2 h. The reaction mixture was partitioned between H$_2$O and EtOAc and the combined EtOAc extracts were dried, filtered and evaporated in vacuo. The crude product was purified by SiO$_2$ chromatography eluting with 25% EtOAc/hexane to afford 50a.

step 1—A mixture of 50a (300 mg, 1.38 mmol), CBr$_4$ (686 mg, 2.07 mmol) and PPh$_3$ (5.43 mg, 2.07 mmol) in DCM (2 mL) was stirred at RT for 3 h. The reaction mixture was concentrated and then purified by SiO$_2$ chromatography eluting with an EtOAc/hexane gradient (0 to 10% EtOAc) to afford 160 mg (41%) of 50b as a colorless oil.

step 2—Ethylene glycol (0.177 mL, 3.17 mmol) was added to a tube containing a solution of 50b (80 mg, 0.286 mmol) in THF (2 mL) at RT. A catalytic amount of Bu$_4$N$^+$I$^-$ was added. The tube was sealed and the stirred solution heated at 65° C. overnight and then cooled and partitioned between EtOAc and water. The organic layer was separated, dried (MgSO$_4$), filtered and concentrated to afford 120 mg of 50c.

The boronic ester 50d is prepared by palladium-catalyzed coupling of 50c and bis-(pinacolato)diboron (0.934 g, 4 mmol) in accord with the procedure described in step b of example 9. Condensation of 50d and 20c is carried out in accord with the procedure in step 3 of example 2 except 21 is replaced with 50d. Demethylation and debenzylation of the ether protecting groups are carried out in accord with the procedures described in steps 4 and 5 of example 3.

Example 11

2-{(E)-2-[3-tert-Butyl-2-methoxy-5-(2-oxo-2H-pyrazin-1-yl)-phenyl]-vinyl}-5-methanesulfonylamino-benzoic acid methyl ester (I-15)

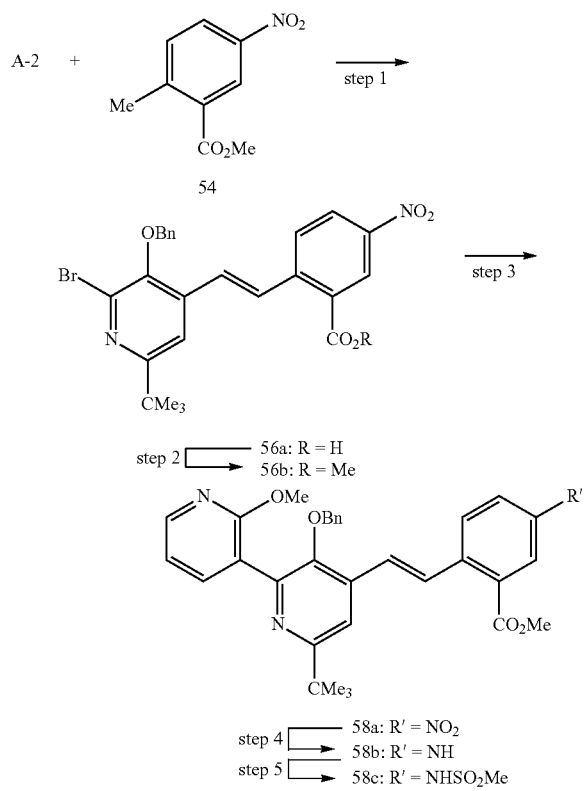

step 1—A solution of A-2 (15.39 mmol), 54 (210.26 mmol), DBU (20.73 mmol) and DMSO (10 mL) is stirred overnight at RT then heated to 50° C. for 1 h. To the solution is added 1N NaOH and the resulting solid filtered. The filtrate is acidified with 6N HCl, extracted with EtOAc, and the combined extracts dried (Na$_2$SO$_4$), filtered and evaporated to afford 56a.

step 2—A solution of 56a (4.608 mmol) iodomethane (16.87 mmol), K$_2$CO$_3$ (13.89 mmol) and DMF (10 mL) is stirred overnight at RT. The resulting solution is filtered and the filtrate is diluted with EtOAc and washed with 1N HCl, H$_2$O and brine. The organic phase is dried (Na$_2$SO$_4$), filtered and concentrated in vacuo to afford 56b.

step 3 is carried out in accord with the procedure described in step 6 of example 1 to afford 58a.

step 4—To a solution of 58a (3.18 mmol) in DMF (10 mL) and EtOAc (10 mL) is added SnCl$_2$ (12.72 mmol) and the resulting solution is stirred at RT overnight. The reaction mixture is cooled to 0° C. and quenched by slow addition of aq. NaHCO$_3$ (4 mL). The resulting suspension is filtered through a pad of CELITE and the filtrate diluted with EtOAc, thrice washed with brine, dried (Na$_2$SO$_4$), filtered and concentrated in vacuo. The crude product is purified by SiO$_2$ chromatography to afford 58b.

Sulfonylation of 58b (step 5) is carried out in accord with the procedure described in step 8 of example 1 to afford 58c. The preparation of methyl 2-[(E)-2-(6-tert-butyl-2'-oxo-1',2'-dihydro-[2,3']bipyridinyl-4-yl)-vinyl]-5-methanesulfonylamino-benzote is completed in accord with the procedures in steps 9-11 of example 1.

Example 12

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 µg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 µL enzymatic reaction contained 20 nM RNA template derived from the complementary sequence of the Internal Ribosome Entry Site (cIRES), 20 nM NS5B570n-Con1 enzyme, 0.5 µCi of tritiated UTP (Perkin Elmer catalog no. TRK-412; specific activity: 30 to 60 Ci/mmol; stock solution concentration from 7.5×10-5 M to 20.6×10-6 M), 1 µM each ATP, CTP, and GTP, 40 mM Tris-HCl pH 8.0, 40 mM NaCl, 4 mM DTT (dithiothreitol), 4 mM MgCl2, and 5 µl of compound serial diluted in DMSO. Reaction mixtures were assembled in 96-well filter plates (cat #MADVNOB, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data was analyzed in Excel® (Microsoft) and ActivityBase® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% ($IC_{50}$) was calculated by fitting equation (i) to the data where "Y"

$$Y = \% \text{ Min} + \frac{(\% \text{ Max} - \% \text{ Min})}{\left[1 + \frac{X}{(IC_{50})^S}\right]} \quad (i)$$

corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

Example 13

HCV Replicon Assay

This assay measures the ability of the compounds of formula Ito inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and *luciferase* activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 µL of phosphate buffered saline (pH 7.0) (PBS) per well and lysed with 20 µL of 1×*R. luciferase* Assay lysis buffer prior to incubation at room temperature for 20 min. The plate was then inserted into the Centro LB 960 microplate luminometer (Berthold Technologies), and 100 µL of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the *luciferase* activity vs. drug concentration as described above.

WST-1 reagent from Roche Diagnostic (cat no. 1644807) was used for the cytotoxicity assay. Ten µL of WST-1 reagent was added to each well of the transparent plates including wells that contain media alone as blanks Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE II

| Compound Number | HCV Replicon Activity $IC_{50}$ (µM) | Cytotoxic Activity $CC_{50}$ (µM) |
| --- | --- | --- |
| I-1 | 0.1081 | 15.1 |
| I-3 | 0.566 | — |

Example 14

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I wherein:

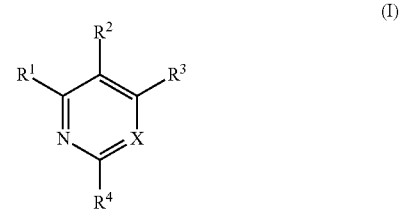

(I)

$X$ is $CR^5$;

$R^1$ is A-1 optionally substituted by halogen, $C_{1-6}$ alkyl, $C_{1-3}$ haloalkyl, $C_{1-6}$ alkoxy:

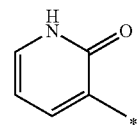

A-1

$R^2$ is hydrogen, cyano or hydroxyl;

$R^3$ is CH=CHAr, $[C(R^6)_2]_n$, naphthyl or C(=O)$X^2$ wherein Ar is phenyl and said phenyl or said naphthyl are optionally independently substituted with one to three substitutents selected from the group consisting of (a) hydroxy, (b) $C_{1-6}$ alkoxy, (c) $C_{1-6}$ alkyl, (d) $C_{1-10}$ hydroxyalkyl wherein one or two carbon atoms optionally can be replaced by oxygen provided that the replacement does not form a oxygen-oxygen bond, (e) $C_{1-3}$ alkoxy-$C_{1-6}$ alkyl, (f) halogen, (g) cyano, (h) $C_{1-6}$ alkoxycarbonyl, (i) $C_{1-6}$ alkylsulfonyl, (j) $X^1(CH_2)_1$— wherein $X^1$ is O, $NR^6$ or a bond, (k) $C_{1-3}$ acylamino-$C_{1-6}$ alkyl, (l) $(CH_2)_nNR^aR^b$ wherein n is zero to two, and (m) carboxyl;

$R^a$ and $R^b$ are (i) independently in each occurrence (a) hydrogen, (b) $C_{1-6}$ alkyl, (c) $C_{1-6}$ alkylsulfonyl, (d) $C_{1-6}$ acyl, (e) $C_{1-6}$ haloalkylsulfonyl, (f) $C_{3-7}$ cycloalkylsulfonyl, (g) $C_{3-7}$ cycloalkyl-$C_{1-3}$ alkyl-sulfonyl, (h) $C_{1-6}$ alkoxy-$C_{1-6}$ alkylsulfonyl, (i) $SO_2NR_6$ or (k) $C_{1-6}$ haloalkyl; $X^2$ is OH, $C_{1-6}$ alkoxy or $NR^cR^d$;

$R^c$ and $R^d$ are (i) independently in each occurrence hydrogen, $C_{1-6}$ alkyl or $C_{4-6}$ cycloalkyl or (ii) taken together with the nitrogen to which they are attached are a cyclic amine wherein the cycloalkyl or cyclic amine moiety is substituted by $(CH_2)_n NR^a R^b$ wherein n is zero to two;

$R^4$ is hydrogen, $C_{1-6}$ alkyl, $C_{1-6}$ haloalkyl, or $CR^{4a}R^{4b}R^{4c}$ wherein (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxy; or (ii) when taken together, $R^{4a}$ and $R^{4b}$ together are $C_{2-4}$ alkylene and $R^{4c}$ is hydrogen, $C_{1-3}$ alkyl, $C_{1-2}$ alkoxy, halogen, $C_{1-3}$ hydroxyalkyl, cyano or $C_{1-3}$ fluoroalkyl;

$R^5$ is hydrogen, $C_{1-6}$ alkoxy, halogen or $C_{1-6}$ alkyl;

$R^6$ is independently in each occurrence hydrogen or $C_{1-3}$ alkyl; or, a pharmaceutically acceptable salt thereof.

2. A compound according to claim 1 wherein:
$X$ is $CR^5$;
$R^5$ is hydrogen;
$R^3$ is $CH=CHAr$ or $[C(R^6)_2]_n$;
Ar is optionally substituted p-phenylene-$(NR^a R^b)$;
$R^4$ is hydrogen, $C_{1-6}$ alkyl, $C_{1-6}$ haloalkyl, or $CR^{4a}R^{4b}R^{4c}$ wherein (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl.

3. A compound according to claim 2 wherein $R^1$ is 2-oxo-1,2-dihydro-pyridin-3-yl and $R^4$ is $CR^{4a}R^{4b}R^{4c}$ wherein $R^{4a}$, $R^{4b}$ and $R^{4c}$ are independently $C_{1-3}$ alkyl.

4. A compound according to claim 3 wherein $R^3$ is $CH=CHAr$; Ar is optionally substituted p-phenylene-$(NR^a R^b)$; $R^a$ is hydrogen and $R^b$ is $C_{1-6}$ alkylsulfonyl.

5. A compound according to claim 1 wherein:
$X$ is $CR^5$;
$R^5$ is hydrogen;
$R^3$ is $C(=O)X^2$;
$X^2$ is OH, $C_{1-6}$ alkoxy or $NR^c R^d$;
$R^4$ is hydrogen, $C_{1-6}$ alkyl, $C_{1-6}$ haloalkyl, or $CR^{4a}R^{4b}R^{4c}$ wherein $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl.

6. A compound according to claim 5 wherein $X^2$ is $NR^c R^d$ and wherein $R^c$ is hydrogen and $R^d$ is a $C_{4-6}$ cycloalkyl substituted by $(CH_2)_n NR^a R^b$ wherein n is zero to two.

7. A compound according to claim 1 wherein:
$X$ is $CR^5$;
$R^5$ is hydrogen;
$R^3$ is optionally substituted naphthyl;
$R^4$ is hydrogen, $C_{1-6}$ alkyl, $C_{1-6}$ haloalkyl, or $CR^{4a}R^{4b}R^{4c}$ wherein: (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxyl.

8. A compound according to claim 7 wherein $R^3$ is 6-methanesulfonylamino-naphthalen-2-yl.

9. A compound selected from the group consisting of:
6-tert-butyl-3-cyano-2'-oxo-1',2'-dihydro-[2,3']bipyridinyl-4-carboxylic acid methyl ester;
6-tert-butyl-3-cyano-2'-oxo-1',2'-dihydro-[2,3']bipyridinyl-4-carboxylic acid (4-methanesulfonylamino-cyclohexyl)-amide;
N-{4-[2-(6-tert-butyl-3-cyano-2'-oxo-1',2'-dihydro-[2,3]bipyridinyl-4-yl)-ethyl]-phenyl}-methanesulfonamide;
N-{4-[(E)-2-(6-tert-butyl-3-hydroxy-2'-oxo-1',2'-dihydro-[2,3]bipyridinyl-4-yl)-vinyl]-phenyl}-methanesulfonamide;
N-{4-[2-(6-tert-butyl-3-hydroxy-2'-oxo-1',2'-dihydro-[2,3]bipyridinyl-4-yl)-ethyl]-phenyl}-methanesulfonamide; and,
N-{4-[(E)-2-(6-tert-butyl-2'-oxo-1',2'-dihydro-[2,3]bipyridinyl-4-yl)-vinyl]-phenyl}-methanesulfonamide.

10. A pharmaceutical composition comprising a compound according to claim 1 admixed with at least one pharmaceutically acceptable carrier, diluent or excipient.

11. A method for treating a Hepatitis C Virus (HCV) infection comprising administering to a patient in need thereof, a therapeutically effective quantity of a compound according to claim 1.

12. The method of claim 11 further co-comprising administering at least one immune system modulator and/or at least one antiviral agent that inhibits replication of HCV.

13. The method of claim 12 wherein the immune system modulator is an interferon, interleukin, tumor necrosis factor or colony stimulating factor.

14. The method of claim 13 wherein the immune system modulator is an interferon or chemically derivatized interferon.

15. The method of claim 12 wherein the antiviral compound is selected from the group consisting of a HCV protease inhibitor, another HCV polymerase inhibitor, a HCV helicase inhibitor, a HCV primase inhibitor and a HCV fusion inhibitor.

16. A method for inhibiting replication of HCV in a cell be delivering a compound according to claim 1.

\* \* \* \* \*